Figure 1:
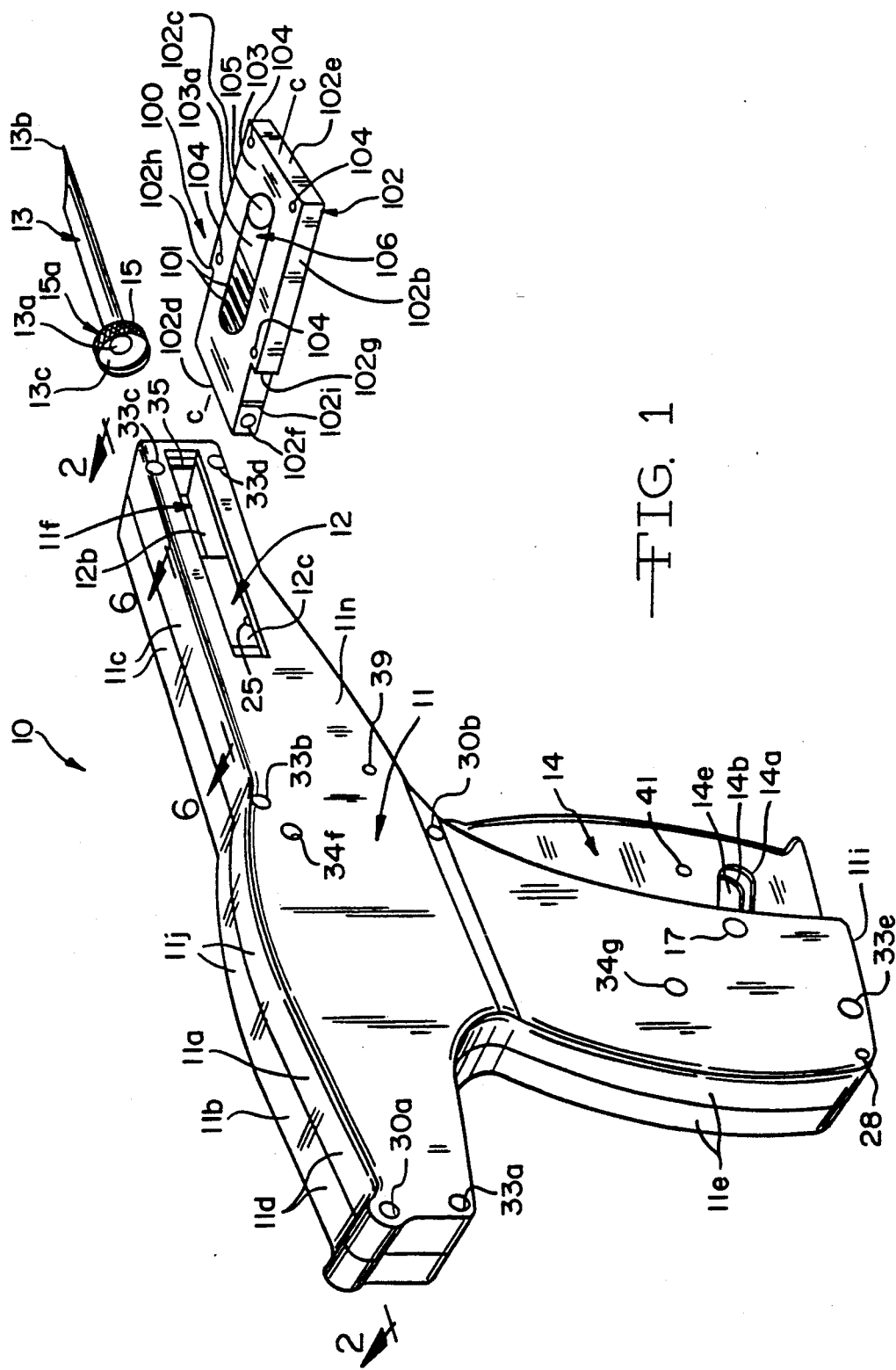

United States Patent [19]

Stewart

[11] Patent Number: 5,147,295
[45] Date of Patent: Sep. 15, 1992

[54] RETRACTABLE IMPLANTER
[75] Inventor: R. Glen Stewart, Lake Villa, Ill.
[73] Assignee: Ideal Instruments, Inc., Chicago, Ill.
[21] Appl. No.: 644,531
[22] Filed: Jan. 23, 1991
[51] Int. Cl.⁵ .......................................... A61M 31/00
[52] U.S. Cl. .................................. 604/61; 604/62; 604/64
[58] Field of Search ................ 604/57, 59-64, 604/72

[56] References Cited
U.S. PATENT DOCUMENTS

| | | | |
|---|---|---|---|
| 3,402,712 | 9/1968 | Eisenhand | 604/61 |
| 4,105,030 | 8/1978 | Kercso | 128/217 |
| 4,154,239 | 5/1979 | Turley | 128/217 |
| 4,451,254 | 5/1984 | Dinius | 604/62 |
| 4,474,572 | 10/1984 | McNaughton | 604/63 |
| 4,687,465 | 8/1987 | Prindle et al. | 604/61 |

Primary Examiner—Robert A. Hafer
Assistant Examiner—David Kenealy
Attorney, Agent, or Firm—Ian C. McLeod

[57] ABSTRACT

An implanting gun apparatus (10) is described. A drive rod (23) is linearly moveable in a handle assembly (11) by a first pivotable linkage (16) actuated by a trigger (14), to urge a pellet (101) from a carrier (100) through a head assembly (12) and into a needle (13). A second pivotable linkage (24), also actuated by the trigger, retracts the needle, the head assembly, and the carrier into the handle after the pellet has been urged into the needle. The gun apparatus is particularly adapted to implant pellets in animals, particularly as medicament pellets.

25 Claims, 5 Drawing Sheets

RETRACTABLE IMPLANTER

BACKGROUND OF THE INVENTION

(1) Field of the Invention

The present invention relates to a pellet implanting gun apparatus for subcutaneously implanting medicament containing pellets into animals without damaging the pellets. More specifically, the invention relates to a pellet implanting gun apparatus which provides for dual actuating means actuated by a trigger. Following insertion of the needle into the animal, the first actuating means urges the pellet through a needle and into the in vivo site of choice. Thereafter, the second actuating means mechanically retracts the needle from the animal leaving behind the first actuating means momentarily. The pellet is thus implanted in the animal, unobstructed by the needle so that there is no chance of damaging the pellet while manually removing the needle from the animal. This permits tissue, which is elastic, to close down over the pellet and to hold the pellet in place.

In other implanters of the prior art, a lot of pressure is placed on pellets during implanting and the pellets have a tendency to become pulverized, cracked, or otherwise damaged during the implanting process. This is especially true during the time when the needle is being manually removed from the insertion site. The present invention overcomes this problem by mechanically retracting the needle from around the pellet immediately after the pellet is implanted in the animal while simultaneously permitting the first actuating means to remain in situ until the hollow needle is withdrawn. This greatly reduces pellet damage during implanting and represents a significant improvement over the prior art.

(2) Prior Art

The prior art has described various types of pellet implant devices. These devices are designed to either retract the pellet drive rod from the needle after the pellets have been urged into the needle or they are designed to only retract the needle from the animal after the drive rod has urged the pellets into the needle. Illustrative of the prior art pellet implant apparatuses are U.S. Pat. No. 4,105,030 to Kercso; U.S. Pat. No. 4,154,239 to Turley and U.S. Pat. No. 4,687,465 to Prindle et al.

Kercso describes an implant apparatus comprised of a track mounted on a handle providing a front and a back track support. A detachable needle is mounted on the front of a retractable carriage that moves along the track. A passageway through the needle corresponds with a passageway through the carriage. A drive rod detachably attaches to the back track support so that the drive rod extends through the carrier passageway and partially through the needle. At least one pellet is placed in the needle passageway adjacent to the drive rod. The needle is then thrust into an animal and a pivotable trigger on the handle is squeezed which releases a propulsion device which retracts the needle from the animal. The drive rod is then manually pulled from the animal, leaving the pellet behind. Before the drive rod is pulled from the animal, there is a great likelihood that the animal will move, often violently, which can cause the pellet to become damaged by the drive rod.

Turley describes a pellet implanter comprised of a trigger pivotably attached to a housing which supports a hollow needle at a forward end. A plunger pin mounted on a shuttle is provided on the housing with the plunger pin aligned to pass through the needle. Pellets are positioned in a chamber between the needle and the plunger pin while a flexible cord extends from one end of the shuttle to the top of the trigger. The needle is inserted into an animal and when the trigger is squeezed, the cord pulls the plunger pin through the pellet chamber and into the needle. The needle is then manually extracted from the animal, leaving the pellets behind. A return spring, secured between the back of the shuttle and the housing causes the plunger pin to be extracted from the needle when the handle is released. Manually extracting the needle from the animal is known to cause the pellets to sometimes crack or become pulverized.

Prindle describes a pellet implanter apparatus comprised of a handle assembly that provides for a drive rod that is linearly moveable in a pistol grip by a pivotable linkage between a trigger and a holder for the drive rod. The proximal end of the linkage has a slot which slides on a roller bearing on the trigger and a distal end which is in slideable relationship through the holder for the drive rod. The proximal end of the linkage rotates in an arc on the roller bearing in the slot while the linkage pivots on a pin on the trigger in an arcuate slot in the trigger against the tension of a spring. When the trigger is squeezed, the distal end of the linkage pushes the rod holder and the drive rod out of the handle assembly, through an opening in a pellet carrier and out of a barrel of a needle to implant a pellet. The implanter apparatus is particularly adapted to implant pellets in animals, particularly as medicament pellets.

OBJECTS

It is therefore an object of the present invention to provide an improved pellet implanting gun apparatus which greatly reduces the risk of the needle and drive rod from damaging a medicament pellet during implanting into an animal. Further, it is an object of the present invention to provide an improved pellet implanting gun apparatus with dual linkage means wherein the first linkage means mechanically urges a drive rod and a medicament pellet into a needle inserted into an animal while the second linkage means is mechanically retracting the needle from the animal Further, it is an object of the present invention to provide an improved pellet implanting gun apparatus with dual linkage means, one for urging the drive rod and medicament pellets into the needle and the other for retracting the needle from the animal after the pellets have entered the needle, wherein each linkage means is comprised of linkage members pivotably joined together in a sturdy construction which is able to withstand continuous use without becoming loose or developing "play" between the linkage members. Still further, it is an object of the present invention to provide a simply constructed, reliable pellet implanting gun apparatus which is inexpensive to manufacture. These and other objects will become increasingly apparent by reference to the following description and to the drawings

IN THE DRAWINGS

FIG. 1 is a right side isometric view of the pellet implanting gun apparatus 10 particularly illustrating a handle 11, a head assembly 12 which mounts a carrier 100 with pellets 101, a needle 13 and a trigger 14.

Figure 2:
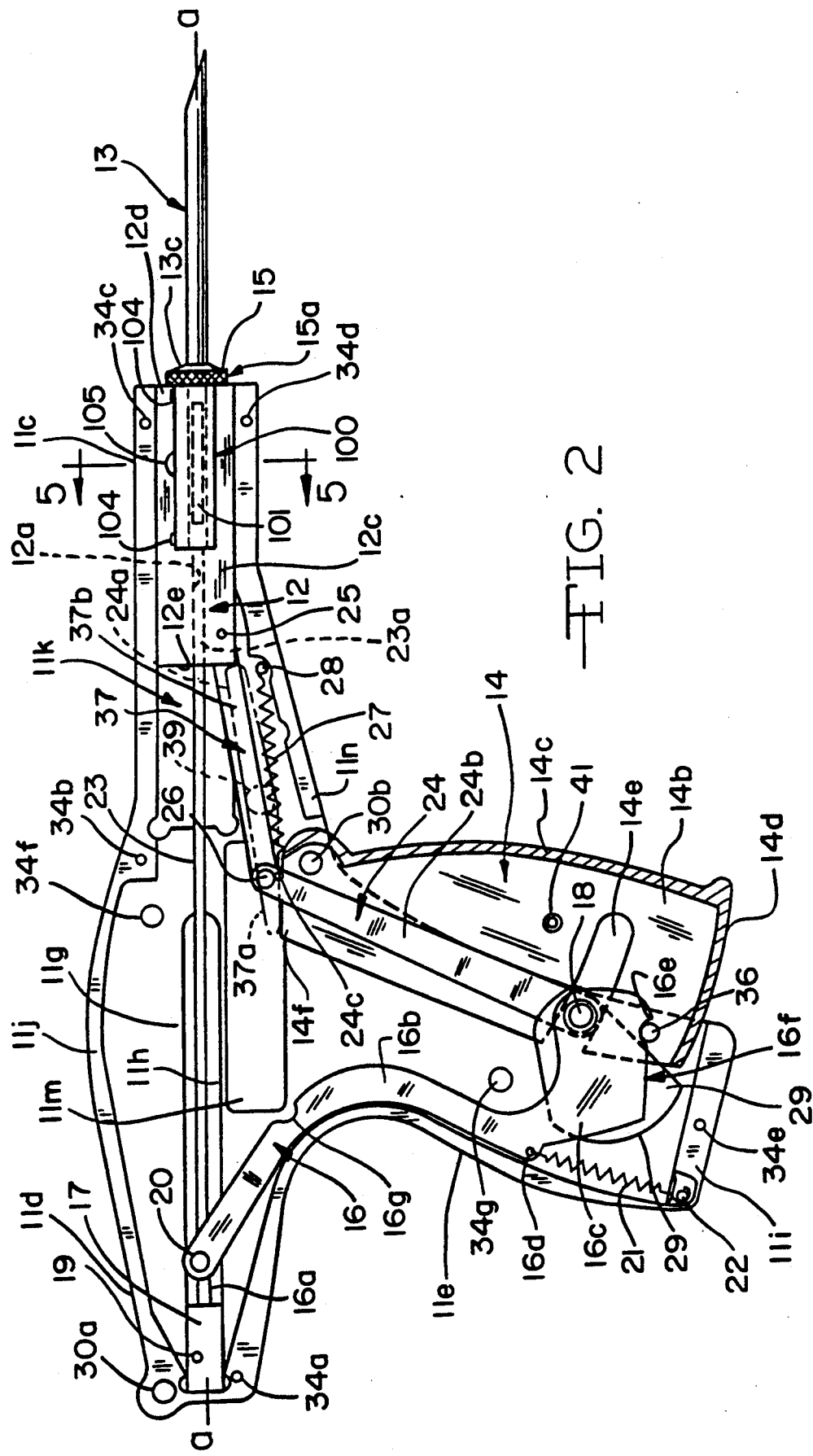
Figure 3:
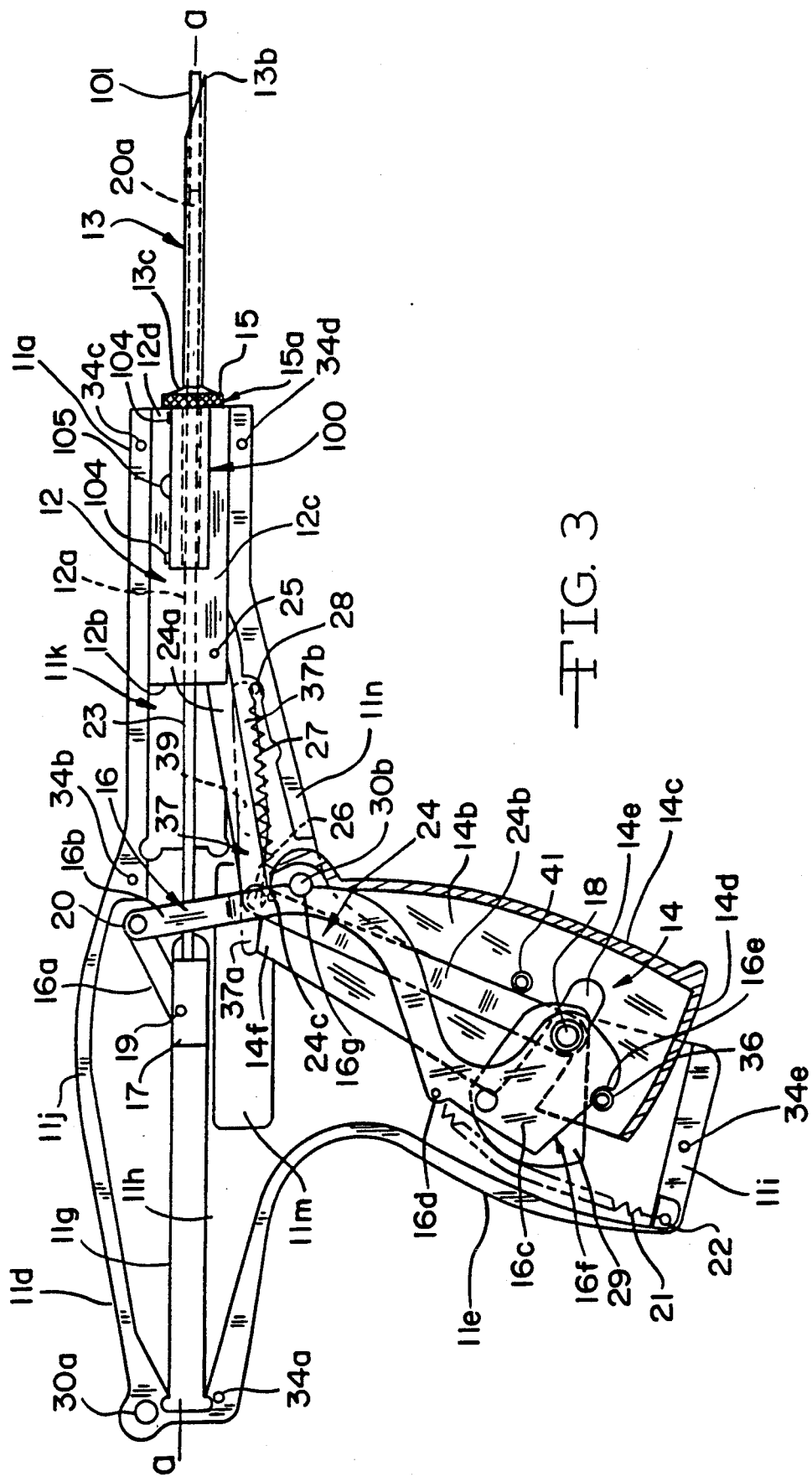

FIG. 2 is a right side, front cross-sectional view along line 2—2 of FIG. 1 showing the trigger 14 and actuated linkages 16 and 24 which connect to the head assembly 12 and a drive rod 23 in the rest position FIG. 3 is a right side, front view of the pellet implanting gun apparatus 10 showing the trigger 14 partially depressed wherein the pivotable linkage 16 has actuated the drive rod 23 and pellet 101 through the head assembly 12 and into the barrel 13.

Figure 4:
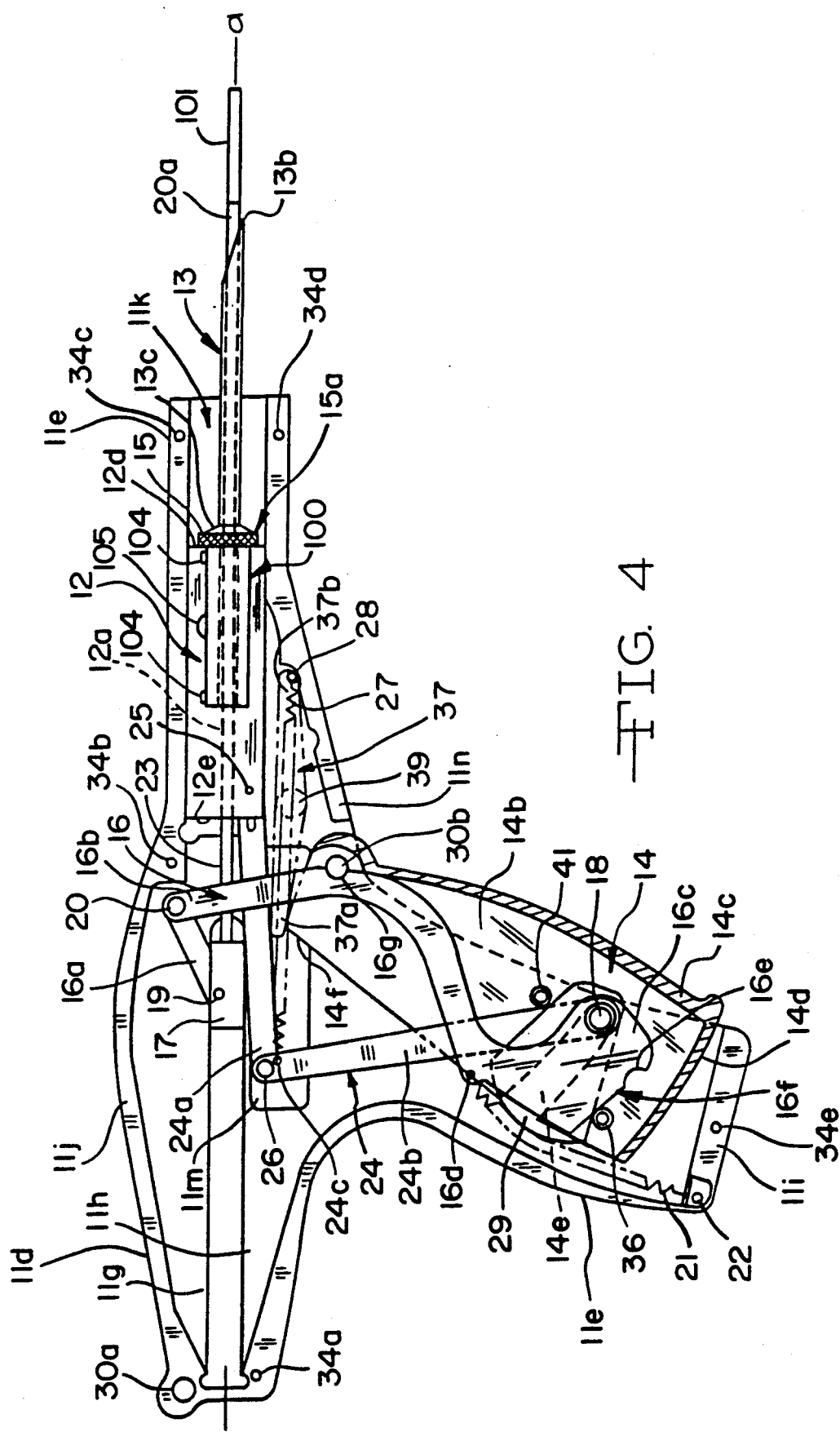

FIG. 4 is a right side, front view of the pellet implanting gun apparatus 10 showing the trigger 14 fully depressed wherein the pivotable linkage 24 has actuated the head assembly 12 to pull the needle 13 into the handle 11.

Figure 5:
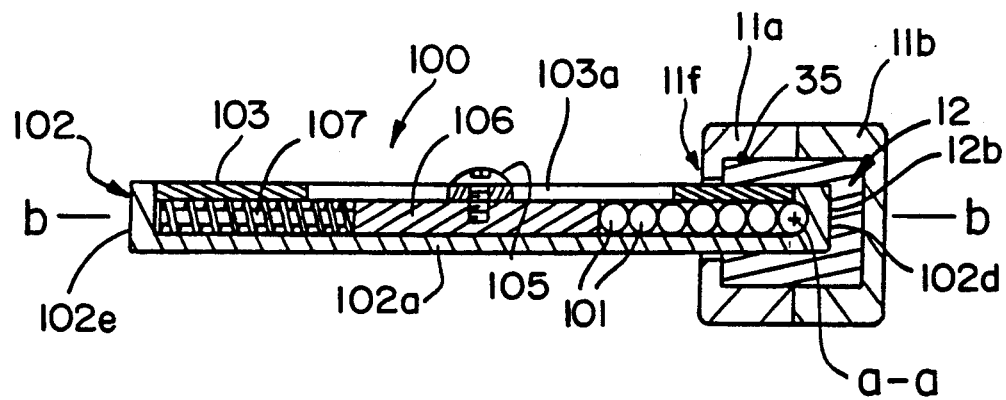

FIG. 5 is a cross-sectional view along line 5—5 of FIG. 2 showing the carrier 100 with pellets 101 inserted into the head assembly 12.

Figure 6:
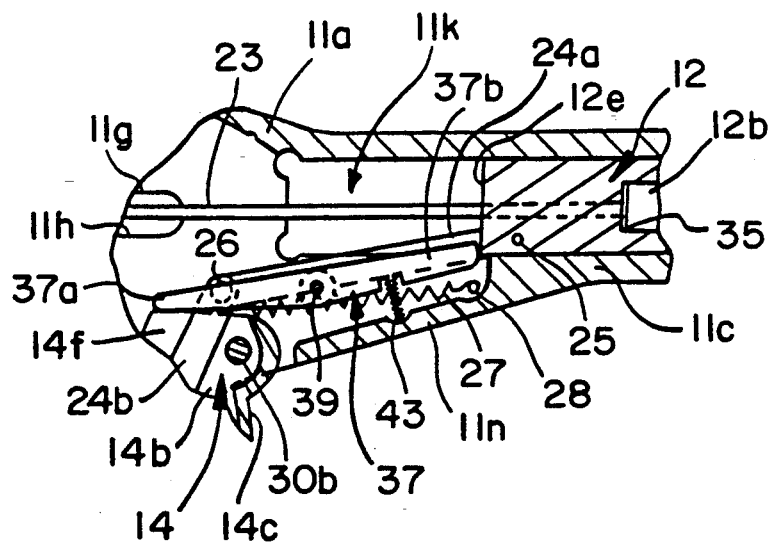

FIG. 6 is a cross-sectional view along line 6—6 of FIG. 1 showing a locking lever 37 holding the head assembly 12 in the handle 11.

GENERAL DESCRIPTION

The present invention relates to a hand held gun apparatus for implanting a pellet into an animal which comprises: a hollow needle having a barrel for implanting the pellet into the animal along a longitudinal axis of the needle; a head means linearly moveable in the gun apparatus along the axis, the head means supporting the needle with an opening through the head means and into the barrel of the needle; a carrier for a pellet mounted at the opening in the head means for holding the pellet in the opening so that the pellet can pass through the barrel of the needle; a pistol grip means supporting the head means; a drive rod linearly moveable through the opening in the head means and into the barrel of the needle along the axis from the pistol grip; a first actuating means mounted in the pistol grip for moving the drive rod; a second actuating means mounted in the pistol grip for moving the head means; and trigger means mounted on the pistol grip and actuatable by the fingers for moving the first actuating means and the second actuating means, wherein the first actuating means moves the drive rod through the opening in the head means and into the barrel of the needle and wherein the second actuating means moves the needle and head means into the pistol grip after the drive rod has moved into the barrel of the needle.

Further, the present invention relates to a hand held gun apparatus for implanting a pellet into an animal which comprises: a hollow needle defining a barrel for implanting the pellet into the animal along a longitudinal axis of the needle; a head means linearly moveable in the gun apparatus along the axis and supporting the needle at a first end and having a second end opposite the first end traversed by an opening along the axis through the head means and into the barrel of the needle; a carrier for a plurality of pellets mounted at the opening in the head means for holding the pellets in the opening so that the pellets can pass through the barrel of the needle; a pistol grip means supporting the head means; a drive rod linearly moveable through the opening between the opposed ends of the head means and into the barrel of the needle along the axis from the pistol grip means; a first actuating means mounted inside of the pistol grip and attached to the drive rod; a second actuating means mounted in the pistol grip and attached to the head assembly; and trigger means mounted on the pistol grip and actuatable by the fingers for moving the first actuating means and the second actuating means, wherein the trigger means engages a first linkage means forming the first actuating means for moving the drive rod through the opening in the head means and into the barrel and wherein the trigger means engages a second linkage means forming the second actuating means for moving the head means and the needle into the pistol grip after the drive rod has moved into the barrel of the needle.

SPECIFIC DESCRIPTION

FIGS. 1 to 6 show a pellet implanting gun apparatus 10 of the present invention. The preferred form of the gun apparatus 10 includes a handle assembly 11, a head assembly 12 supporting a needle 13 and a trigger 14. The handle assembly 11 includes a right half 11a and a left half 11b (FIG. 1) which are mirror images of each other. The halves 11a and 11b have a nose end 11c, a butt end 11d and a grip portion 11e which receives the trigger 14 when the trigger 14 is actuated. A side slot 11f through the right half 11a of the handle assembly 11 in the nose 11c provides for linear movement of a carrier 100 with pellets 101.

The head assembly 12 has a rectangular cross-section along a plane perpendicular to the axis a—a and provides for a bore 12a (FIG. 3). An opening 12b through the front side 12c of the head assembly 12 is in communication with the bore 12a for positioning the carrier 100 with pellets 101 along the axis a—a (FIG. 5).

The needle 13 has a barrel 13a with an angular taper forming into a pointed tip 13b at one end and a flanged section 13c at the other end. A knurled nut 15 is mounted on the flanged section 13c and secures the needle 13 to the distal end 12d of the head assembly 12 adjacent to the opening 12b. The nut 15 has a gripping outer surface 15a to help remove the needle 13 from the head assembly 12 for changing and cleaning. The trigger 14 is formed of spaced apart plates 14a and 14b (FIG. 1) which are mirror images of each other and which are connected together by a front plate 14c and a bottom plate 14d.

As shown in FIG. 2, when the gun apparatus 10 is in the rest position, a first pivotable linkage 16 extends from a rod holder 17 to a shuttle linkage pivot pin 18 mounted between the two halves 11a and 11b of the handle assembly 11 adjacent to an arcuate slot 14e in the trigger 14. Pivotable linkage 16 is comprised of linkage members 16a and 16b. Linkage member 16a is secured to the rod holder 17 through a securing slot (not shown) offset in front of the axis a—a (FIG. 5) by a roll pin 19 and extends to a linkage pin 20. The linkage pin 20 pivotably secures the linkage member 16a to the linkage member 16b which extends to the shuttle linkage pivot pin 18. The linkage member 16b has a serpentine shape with an enlarged section 16c at its lower end. A return spring 21 is mounted between an opening 16d adjacent to the enlarged section 16c and a securing post 22 mounted in the bottom 11i of the handle assembly 11 to hold the linkage members 16a and 16b in the rest position. The return spring 21 serves to return the first pivotable linkage 16 and a drive rod 23 mounting the rod holder 17 to their respective rest positions after the gun apparatus 10 has been activated to release a pellet 101.

A second pivotable linkage 24, comprised of linkage members 24a and 24b, extends from the proximal end 12e of the head assembly 12 to the shuttle link pivot pin 18. Linkage member 24a is secured to the proximal end 12e of the head assembly 12, offset behind the axis a—a (FIG. 5) in a securing slot (not shown) by a roll pin 25 and extends to a linkage pin 26. Linkage pin 26 pivotably secures the linkage member 24a to the linkage member 24b which extends to the shuttle linkage pivot pin 18.

When the trigger 14 is in the rest position (FIG. 2), the drive rod 23 is positioned between the bore 12a in the head assembly 12 and the butt end 11d of the handle assembly 11. The drive rod 23 is linearly slideable along the axis a—a through the bore 12a and into the barrel 13a of needle 13. The drive rod 23 is moved along parallel side rails 11g and 11h on each half 11a and 11b of the handle assembly 11 by the rod holder 17 which slides between the rails 11g and 11h. A return spring 27 is mounted between an opening 24c in linkage member 24b adjacent to linkage pin 26 and a securing post 28 adjacent to the proximal end 12e of the head assembly 12 when the head assembly 12 is at rest. The return spring 27 serves to return the second pivotable linkage 24 and the head assembly 12 to their respective rest positions after the gun apparatus 10 has been fired.

A rounded back rest member 29 preferably made of teflon, is provided on shuttle linkage pivot pin 18 between linkage member 16b of the first pivotable linkage 16 and linkage member 24b of the second pivotable linkage 24. Rest member 29 serves both to reduce the wear on return spring 21 against the enlarged section 16c of pivotable linkage 16 and to reduce the sliding friction between the enlarged section 16c and linkage member 24b of the second pivotable linkage 24.

The right half 11a and the left half 11b of the handle assembly 11 are assembled together by lining up guide pin 30a, hinge pin 30b and shuttle linkage pivot pin 18. The two halves 11a and 11b are then secured together with set screws 33a, 33b, 33c, 33d and 33e (FIG. 1) through openings 34a, 34b, 34c, 34d and 34e (FIG. 2 to 4). Openings 34f and 34g act as safety mechanisms to prevent the gun apparatus 10 from firing when a guide pin (not shown) is inserted into the openings 34f and 34g.

A carrier 100 with a plurality of pellets 101 is mounted through the side slot 11f in the right half 11a of the handle assembly 11 and into the opening 12b in the front side 12c of the head assembly 12. The carrier 100 has a rectangular cross-section along the axis b—b and comprises a base plate 102 having a bottom wall 102a (FIG. 5) with spaced apart sidewalls 102b and 102c and end wall 102d and 102e between the sidewalls 102b and 102c. The sidewalls 102b and 102c each provide for an opening 102f (only opening 102f through sidewall 102b shown in FIG. 1) adjacent to the end wall 102d that allows the user to fill the carrier 100 with pellets 101 and which also allows the pellets 101 to be ejected from the carrier 100 when the gun apparatus 10 is actuated. The sidewlls 102b and 102c have stepped portions 102g and 102h, respectively, spaced from the opening 102f. The stepped portions 102g and 102h abut against the front side 12c of the head assembly 12 when the carrier 100 is inserted through the side slot 11f and into the front side 12c of the head assembly 12. A top plate 103 is secured to the sidewalls 102b and 102c of the bottom plate 102 by mounting screws 104. The top plate 103 has a slot 103a that provides for movement of a screw 105 threadably mounted in a plate 106 biased by a spring 107 (FIG. 5). The carrier 100 is held in place in the opening 12b in the front side 12c of the head assembly 12 by an inverted U-shaped retaining wire 35 (FIGS. 1, 5 and 6) that snappingly mates with a groove 102i (FIG. 1) in the sidewalls 102b and 102c (only 102b shown) of the carrier 100.

To load the carrier 100, the user slides the screw 105 towards the end wall 102e which compresses the spring 107. Pellets 101 are then inserted through the opening 102f in either sidewall 102b or 102c until the carrier 100 is full of pellets (partially shown in FIG. 5). As the pellets 101 are ejected from the gun apparatus 10, the spring 107 advances the plate 106 and the row of pellets 101 so that the next pellet 101 is positioned along the axis a—a in the opening 102f of the carrier 100 in line with the bore 12a through the head assembly 12 and the drive rod 23 for firing into an animal.

In operation, the pellets 101 are implanted subcutaneously into domestic animals such as cattle, sheep, horses and pigs. The pellets 101 are usually inserted into the animal's ear because an animal's ear has good blood circulation which allows the pellets 101 to effectively dissolve. Because an animal's ear is not consumed by humans, there is also little risk of a human ingesting a partially dissolved pellet 101.

To implant a pellet 101 into an animal, the needle 13 is first inserted into the animal's ear to the desired depth. The trigger 14 is then actuated by squeezing with the fingers. As shown in FIGS. 2 to 4, as the arcuate opening 14e in the trigger 14 moves over the shuttle linkage pivot pin 18, a lever roll pin 36, provided between the spaced apart plates 14a and 14b of the trigger 14 adjacent to the bottom plate 14d, rotates in a semicircular notch 16e in the enlarged section 16c of linkage member 16b before moving over a level surface 16f of the enlarged section 16d. When the force of the fingers squeezing on the trigger 14 is transferred to the linkage member 16b, the enlarged section 16c of linkage member 16b pivots on the shuttle link pivot pin 18, causing linkage member 16b to move towards the nose end 11c of the handle assembly 11. As the linkage member 16b moves forward, the linkage member 16a of the pivotable linkage 16 moves forward as well, stretching the return spring 21 and pulling the rod holder 17 and drive rod 23 forward through the head assembly 12 and into the needle 13. When this occurs, the linkage members 16a and 16b pivot on linkage pin 20 as the rod holder 17 travels substantially the entire distance of the parallel side rails 11g and 11h. The top 11j of the handle assembly 11 is arched to accommodate this movement.

As shown in FIG. 3, the arcuate movement of the linkage member 16b is complete when a semicircular notch 16g in linkage member 16b rests against the hinge pin 30b. At this point, when the lever roll pin 36 has stopped rotating in the semicircular notch 16g and is just beginning to travel over the level surface 16f of the enlarged section 16c, the rod holder 17 has traveled substantially the entire distance down the rails 11g and 11h of the handle assembly 11, and the front end 23a of the drive rod 23 has engaged a pellet 101 in carrier 100 and pushed the pellet 101 out of the bore 12a in the head assembly 12 and through the barrel 13a in needle 13 to the pointed tip 13b at the end of the needle 13. At this time, when the forward movement of the drive rod 23 into the needle 13 is complete, the arcuate opening 14e in trigger 14 has traveled the majority of its arcuate extent over the shuttle linkage pivot pin 18.

As shown in FIGS. 2 and 6, a head assembly lock 37 is mounted on the right half 11a of the handle assembly 11 adjacent to the upper end 14f of trigger 14 and the proximal end 12e of the head assembly 12. The head assembly lock 37 pivots on a fulcrum pin 39 and locks the head assembly 12 in place when the gun apparatus 10 is in the rest position. When the trigger 14 is actuated (FIG. 3), the upper end 14f of the trigger 14, opposite the hinge pin 30b, engages the left arm 37a of the head assembly lock 37, forcing the left arm 37a to pivot upward on fulcrum pin 39 towards the drive rod 23 so that the right arm 37b pivots downward towards the securing post 28, thereby unlocking the head assembly 12. The head assembly 12 is now free to travel backwards in a channel 11k formed in the nose end 11c of the handle assembly 11.

As shown in FIG. 3 when the drive rod 23 has substantially completed its travel through the needle 13, a lever roll pin 41 provided between the spaced apart plates 14a and 14b of the trigger 14 adjacent to the arcuate notch 14e, has just started to engage the linkage member 24b of the second pivotable linkage 24. Further movement of the trigger 14 into the handle assembly 11 causes lever roll pin 41 to force the linkage member 24b to pivot in an arcuate path around the shuttle linkage pivot pin 18. Movement of the linkage member 24b causes linkage member 24a to pivot on linkage pin 26 and move towards the butt end 11d of the handle assembly 11, stretching the return spring 27 and pulling the head assembly 12 and the needle 13 into the gun apparatus 10. The linkage pin 26 travels through a recess 11m provided in the left half 11b of the handle assembly 11 as the head assembly travels substantially the entire length of the channel 11k. The head assembly 12 pulls the pointed tip 13b of needle 13 out of the animal's ear so that the animal tissue, pierced by the needle 13, can close and envelope the pellet 101. The gun apparatus 10 is then pulled away from the animal and the trigger 14 is released.

Releasing the trigger 14 lets the gun apparatus 10 return to its rest position as shown in FIG. 2. This occurs when the return spring 21 unstretches to return the first pivotable linkage 16 and the drive rod 23 with the drive rod holder 17 to their respective rest positions and when the return spring 27 unstretches to return the second pivotable linkage 24 and the head assembly 12 with the needle 13 and the carrier 100 to their respective rest positions. As the head assembly 12 returns to the nose end 11c of the handle assembly 11, a spring 43 (FIG. 6) provided between the right arm 37b of the head assembly lock 37 and the lower section 11n of the nose end 11c of the handle assembly 11, forces the right arm 37b upward so that it locks the head assembly 12 in the rest position.

Once the gun apparatus 10 has returned to its rest position, the spring 107 in carrier 100 advances the plate 106 and the pellets 101 toward the end wall 102d of the carrier 100. This causes another pellet 101 to be registered along the axis a—a in the opening 102f of the carrier 100 in line with the bore 12a through the head assembly 12 and the drive rod 23 for firing into an animal.

Numerous variations will occur to those skilled in the art and it is intended that the present invention be limited only by the hereinafter appended claims.

I claim:

1. A hand held gun apparatus for implanting a pellet into an animal which comprises:
   (a) a hollow needle having a barrel for implanting the pellet into the animal along a longitudinal axis of the needle;
   (b) a head means linearly moveable in the gun apparatus along the axis, the head means supporting the needle with an opening through the head means and into the barrel of the needle;
   (c) a carrier for a pellet mounted at the opening in the head means for holding the pellet in the opening so that the pellet can pass through the barrel of the needle;
   (d) a pistol grip means supporting the head means;
   (e) a drive rod linearly moveable through the opening in the head means and into the barrel of the needle along the axis from the pistol grip means;
   (f) a first, elongate linkage means mounted on the pistol grip means and extending between the drive rod and the trigger means and pivoting on the pistol grip means for moving the drive rod;
   (g) a second, elongate linkage means mounted on the pistol grip means and extending between the head means and the trigger means and pivoting on the pistol grip means for moving the head means; and
   (h) a trigger means mounted on the pistol grip means and actuatable by the fingers of an operator for moving the first linkage means and the second linkage means, wherein the first linkage means moves the drive rod through the opening in the head means and into the barrel of the needle and wherein the second linkage means moves the needle and head means into the pistol grip means after the drive rod has moved into the barrel of the needle.

2. A hand held gun apparatus for implanting a pellet into an animal which comprises:
   (a) a hollow needle having a barrel for implanting the pellet into the animal along a longitudinal axis of the needle;
   (b) a head means linearly moveable in the gun apparatus along the axis and supporting the needle at a first end and having a second end opposite the first end traversed by an opening along the axis through the head means and into the barrel of the needle;
   (c) a carrier for a plurality of pellets mounted at the opening in the head means for holding the pellets in the opening so that the pellets can pass through the barrel of the needle;
   (d) a pistol grip means supporting the head means;
   (e) a drive rod linearly moveable through the opening between the opposed ends of the head means and into the barrel of the needle along the axis from the pistol grip means;
   (f) a first linkage means pivotably mounted on the pistol grip means and attached to the drive rod;
   (g) a second linkage means pivotably mounted on the pistol grip means and attached to the head assembly; and
   (h) a trigger means mounted on the pistol grip means and actuatable by the fingers of an operator for pivoting the first linkage means and the second linkage means, wherein the first linkage means has a first end attached to the drive rod and a second end opposite the first end that is engaged by a first cam means mounted on the trigger means for moving the drive rod through the opening in the head means and into the barrel of the needle and wherein the second linkage means has a first end attached to the second end of the head means and a second end opposite the first end that is engaged by a second cam means mounted on the trigger means for moving the head means and the needle into the pistol grip means with the drive rod moved into the barrel of the needle.

3. The apparatus of claim 2 wherein the first and second linkage means are spring loaded to return the trigger means, the drive rod and the head means to a rest position after the trigger means is released by the fingers of the operator.

4. The apparatus of claim 2 wherein the second end of the first linkage means and the second end of the second linkage means pivotably engage a linkage pivot pin mounted inside and on the pistol grip means.

5. The apparatus of claim 2 wherein the second end of the first linkage means is pivotably mounted on a linkage pivot pin mounted on the pistol grip means and is pivoted by the trigger means adjacent a surface on the first linkage means, which slideably engages a first roller pin mounted on the trigger means as the first cam means and wherein the second end of the second linkage means is pivotably mounted on the linkage pivot pin mounted on the pistol grip means and is pivoted by the trigger means adjacent a surface on the second linkage means, which slideably engages a second roller pin mounted on the trigger means as the second cam means.

6. The apparatus of claim 2 wherein a lever means has spaced apart arms and is pivotably mounted between the arms of the lever means on the pistol grip means and wherein one of the arms of the lever means locks the head means in the pistol grip means and wherein the lever means releases the head means by movement of a surface of the trigger means against an other of the arms of the lever means so that the second linkage means can move the head means and the needle into the pistol grip means.

7. The apparatus of claim 6 wherein the trigger means is pivoted on a pivot means mounted on the pistol grip means adjacent to the head means and the lever means.

8. The apparatus of claim 5 wherein the pistol grip means has opposed sides which mount the linkage pivot pin between the opposed sides and wherein a slot is provided in the trigger means which moves over the linkage pivot pin when the trigger means is actuated.

9. The apparatus of claim 5 wherein the trigger means has opposed sides which mount the first roller pin and wherein the second roller pin is mounted between the sides of the trigger means so that a part of the first linkage means and a part of the second linkage means are moved parallel to and between the opposed sides of the trigger means when the trigger means is actuated between opposed sides of the pistol grip means.

10. The apparatus of claim 2 wherein the first linkage means has a linkage pivot pin between the first and second ends and mounted inside and on the pistol grip means such that when the trigger means is actuated, the trigger means moves the first linkage means which pivots on the linkage pivot pin to move the drive rod linearly through the opening in the head means and into the barrel of the needle and wherein the second linkage means is mounted on the linkage pivot pin between the first and second ends and mounted inside and on the pistol grip means such that as the trigger means is actuated to move the drive rod into the barrel of the needle, the trigger means moves the second linkage means which pivots on the linkage pivot pin to move the head means and the needle linearly into the pistol grip means.

11. The apparatus of claim 5 wherein the first linkage means has a linkage pivot pin between the first and second ends and mounted inside and on the pistol grip means such that when the trigger means is actuated, the trigger means moves the first linkage means which pivots on the linkage pivot pin to move the drive rod linearly through the opening in the head means and into the barrel of the needle and wherein the second linkage means is mounted on the linkage pivot pin between the first and second ends and mounted inside and on the pistol grip means such that as the trigger means is actuated to move the drive rod into the barrel of the needle, the trigger means moves the second linkage means which pivots on the linkage pivot pin to move the head means and the needle linearly into the pistol grip means.

12. The apparatus of claim 2 wherein the first linkage means has a first segment with spaced apart ends and a second segment with spaced apart ends wherein one of the ends of the first and the second segments of the first linkage means are pivotably joined by a first linkage pivot pin and wherein an other of the ends of the first segment of the first linkage means is attached to the drive rod and an other of the ends of the second segment of the first linkage means is pivotably mounted on the linkage pivot pin mounted inside and on the pistol grip means and wherein the second linkage means has a first segment with spaced apart ends and a second segment with spaced apart ends wherein one of the ends of the first and the second segments of the second linkage means are pivotably joined by a second linkage pivot pin and wherein an other of the ends of the first segment of the second linkage means is attached to the second end of the head means and an other of the ends of the second segment of the second linkage means is pivotably mounted on the linkage pivot pin mounted inside and on the pistol grip means such that when the trigger means is actuated, the trigger means causes the second segment of the first linkage means to engage the first cam means mounted on the trigger means to engage the first cam means mounted on the trigger means and to pivot on the linkage pivot pin mounted inside and on the pistol grip means so that the second segment of the first linkage means moves toward the head means which causes the first segment of the first linkage means to move the drive rod linearly through the opening in the head means and into the barrel of the needle and wherein actuation of the trigger means also causes the second segment of the second linkage means to engage the second cam means mounted on the trigger means and to pivot on the linkage pivot pin mounted inside and on the pistol grip means so that the second segment of the second linkage means moves towards the other end of the first segment of the first linkage means attached to the drive rod which causes the first segment of the second linkage means to move the head means and the needle into the pistol grip means after the drive rod has moved into the barrel of the needle.

13. The apparatus of claim 5 wherein the first linkage means has a first segment with spaced apart ends and a second segment with spaced apart ends wherein one of the ends of the first and the second segments of the first linkage means are pivotably joined by a first linkage pivot pin and wherein an other of the ends of the first segment of the first linkage means is attached to the drive rod and an other of the ends of the second segment of the first linkage means is pivotably mounted on the linkage pivot pin mounted inside and on the pistol grip means and wherein the second linkage means has a first segment with spaced apart ends and a second segment with spaced apart ends wherein one of the ends of the first and the second segments of the second linkage means are pivotably joined by a second linkage pivot pin and wherein an other of the ends of the first segment of the second linkage means is attached to the second end of the head means and an other of the ends of the second segment of the second linkage means is pivotably mounted on the linkage pivot pin mounted inside and on the pistol grip means such that when the trigger means is actuated, the trigger means causes the second segment of the first linkage means to engage the first roller pin mounted on the trigger means and to pivot on the linkage pivot pin mounted inside and on the pistol grip means so that the second segment of the first linkage means moves toward the head means which causes the first segment of the first linkage means to move the drive rod linearly through the opening in the head means and into the barrel of the needle and wherein actuation of the trigger means also causes the second segment of the second linkage means to engage the second roller pin mounted on the trigger means and to pivot on the linkage pivot pin mounted inside and on the pistol grip means so that the second segment of the second linkage means moves toward the other end of the first segment of the first linkage means attached to the drive rod which causes the first segment of the second linkage means to move the head means and the needle into the pistol grip means after the drive rod has moved into the barrel of the needle.

14. A method for implanting a pellet into an animal which comprises:
(a) providing a hand held gun apparatus comprising a hollow needle having a barrel for implanting the pellet into the animal along a longitudinal axis of the barrel; a head means linearly moveable in the gun apparatus along the axis and supporting the needle at a first end and having a second end opposite the first end traversed by an opening along the axis through the head means and into the barrel of the needle; a carrier for a plurality of pellets mounted at the opening in the head means for holding the pellets in the opening so that the pellets can pass through the barrel of the needle; a pistol grip means supporting the head means; a drive rod linearly moveable through the opening between the opposed ends of the head means and into the barrel of the needle along the axis from the pistol grip means; a first linkage means pivotably mounted on the pistol grip means and attached to the drive rod; a second linkage means pivotably mounted on the pistol grip means and attached to the head assembly; and a trigger means mounted on the pistol grip means and actuatable by the fingers of an operator for pivoting the first linkage means and the second linkage means, wherein the first linkage means has a first end attached to the drive rod and a second end opposite the first end that is engaged by a first cam means mounted on the trigger means for moving the drive rod through the opening in the head means and into the barrel of the needle and wherein the second linkage means has a first end attached to the second end of the head means and a second end opposite the first end that is engaged by a second cam means mounted on the trigger means for moving the head means and the needle into the pistol grip means with the drive rod moved into the barrel of the needle;
(b) placing a plurality of pellets into the carrier;
(c) inserting the needle into the animal; and
(d) actuating the trigger means with the fingers of the operator wherein the first linkage means moves the drive rod, which urges a pellet from the carrier through the opening in the head means and into the barrel of the needle and wherein the second linkage means moves the head means and the needle into the pistol grip means with the drive rod moved into the barrel of the needle so that the pellet is deposited in the animal without being obstructed by the needle.

15. The method of claim 14 wherein the first and second linkage means are spring loaded to return the trigger means, the drive rod and the head means to a rest position after the trigger means is released by the fingers of the operator.

16. The method of claim 14 wherein the second end of the first linkage means and the second end of the second linkage means pivotably engage a linkage pivot pin mounted inside and on the pistol grip means.

17. The method of claim 14 wherein the second end of the first linkage means is pivotably mounted on a linkage pivot pin mounted on the pistol grip means and is pivoted by the trigger means adjacent a surface on the first linkage means which slideably engages a first roller pin mounted on the trigger means as the first cam means and wherein the second end of the second linkage means is pivotably mounted on the linkage pivot pin mounted on the pistol grip means and is pivoted by the trigger means adjacent a surface on the second linkage means which slideably engages a second roller pin mounted on the trigger means as the second cam means.

18. The method of claim 14 wherein a lever means has spaced apart arms and is pivotably mounted on the pistol grip means between the arms of the lever means and wherein one of the arms of the lever means locks the head means in the pistol grip means and wherein the lever means releases the head means by movement of a surface of the trigger means against an other of the arms of the lever means when the trigger means is actuated by the fingers of the operator for moving the first linkage means so that the second linkage means can move the head means and the needle into the pistol grip means.

19. The method of claim 18 wherein the trigger means is pivoted on a pivot means mounted on the pistol grip means adjacent to the head means and the lever means.

20. The method of claim 17 wherein the pistol grip means has opposed sides which mount the linkage pivot pin between the opposed sides and wherein a slot is provided in the trigger means which moves over the linkage pivot pin when the trigger means is actuated.

21. The method of claim 17 wherein the trigger means has opposed sides which mount the first roller pin and wherein the second roller pin is mounted between the sides of the trigger means so that a part of the first linkage means and a part of the second linkage means are moved parallel to and between the opposed sides of the trigger means when the trigger means is actuated between opposed sides of the pistol grip means.

22. The method of claim 14 wherein the first linkage means has a linkage pivot pin between the first and second ends and mounted inside and on the pistol grip means such that when the trigger means is actuated, the trigger means moves the first linkage means which pivots on the linkage pivot pin to move the drive rod linearly through the opening in the head means and into the barrel of the needle and wherein the second linkage means is mounted on the linkage pivot pin between the first and second ends and mounted inside and on the pistol grip means such that as the trigger means is actuated to move the drive rod into the barrel of the needle, the trigger means moves the second linkage means which pivots on the linkage pivot pin to move the head means and the needle linearly into the pistol grip means.

23. The method of claim 17 wherein the first linkage means has a linkage pivot pin between the first and second ends and mounted inside and on the pistol grip means such that when the trigger means is actuated, the trigger means moves the first linkage means which pivots on the linkage pivot pin to move the drive rod linearly through the opening in the head means and into the barrel of the needle and wherein the second linkage means is mounted on the linkage pivot pin between the first and second ends and mounted inside and on the pistol grip means such that as the trigger means is actuated to move the drive rod into the barrel of the needle, the trigger means moves the second linkage means which pivots on the linkage pivot pin to move the head means and the needle linearly into the pistol grip means.

24. The method of claim 14 wherein the first linkage means has a first segment with spaced apart ends and a second segment with spaced apart ends wherein one of the ends of the first segment of the first linkage means and one of the ends of the second segment of the first linkage means are pivotably joined by a first linkage pivot pin and wherein an other of the ends of the first segment of the first linkage means is attached to the drive rod and an other of the ends of the second segment of the first linkage means is pivotably mounted on the linkage pivot pin mounted inside and on the pistol grip means and wherein the second linkage means has a first segment with spaced apart ends and a second segment with spaced apart ends wherein one of the ends of the first segment of the second linkage means and one of the ends of the second segment of the second linkage means are pivotably joined by a second linkage pivot pin and wherein an other of the ends of the first segment of the second linkage means is attached to the second end of the head means and an other of the ends of the second segment of the second linkage means is pivotably mounted on the linkage pivot pin mounted inside and on the pistol grip means such that when the trigger means is actuated, the trigger means causes the second segment of the first linkage means to engage the first cam means mounted on the trigger means and to pivot on the linkage pivot pin mounted inside and on the pistol grip means so that the second segment of the first linkage means moves toward the head means which causes the first segment of the first linkage means to move the drive rod linearly through the opening in the head means and into the barrel of the needle and wherein actuation of the trigger means also causes the second segment of the second linkage means to engage the second cam means mounted on the trigger means and to pivot on the linkage pivot pin mounted inside and on the pistol grip means so that the second segment of the second linkage means moves toward the other end of the first segment of the first linkage means attached to the drive rod which causes the first segment of the second linkage means to move the head means and the needle into the pistol grip means after the drive rod has moved into the barrel of the needle.

25. The method of claim 17 wherein the first linkage means has a first segment with spaced apart ends and a second segment with spaced apart ends wherein one of the ends of the first segment of the first linkage means and one of the ends of the second segment of the first linkage means are pivotably joined by a first linkage pivot pin and wherein an other of the ends of the first segment of the first linkage means is attached to the drive rod and an other of the ends of the second segment of the first linkage means is pivotably mounted on the linkage pivot pin mounted inside and on the pistol grip means and wherein the second linkage means has a first segment with spaced apart ends and a second segment with spaced apart ends wherein one of the ends of the first segment of the second linkage means and one of the ends of the second segment of the second linkage means are pivotably joined by a second linkage pivot pin and wherein an other of the ends of the first segment of the second linkage means is attached to the second end of the head means and an other of the ends of the second segment of the second linkage means is pivotably mounted on the linkage pivot pin mounted inside and on the pistol grip means such that when the trigger means is actuated, the trigger means causes the second segment of the first linkage means to engage the first roller pin mounted on the trigger means and to pivot on the linkage pivot pin mounted inside and on the pistol grip means so that the second segment of the first linkage means moves toward the head means which causes the first segment of the first linkage means to move the drive rod linearly through the opening in the head means and into the barrel of the needle and wherein actuation of the trigger means also causes the second segment of the second linkage means to engage the second roller pin mounted on the trigger means and to pivot on the linkage pivot pin mounted inside and on the pistol grip means so that the second segment of the second linkage means moves toward the other end of the first segment of the first linkage means attached to the drive rod which causes the first segment of the second linkage means to move the head means and the needle into the pistol grip means after the drive rod has moved into the barrel of the needle.

* * * * *